US009683935B2

(12) United States Patent
e Silva et al.

(10) Patent No.: US 9,683,935 B2
(45) Date of Patent: Jun. 20, 2017

(54) METHOD TO MEASURE SURFACTANT IN FLUID

(75) Inventors: Viviane Pacheco e Silva, Sao Paulo (BR); Luiz Wanderley Bratfisch Pace, Sao Paulo (BR); Edmir Carone, Jr., Sao Paulo (BR)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 13/525,395

(22) Filed: Jun. 18, 2012

(65) Prior Publication Data
US 2013/0337568 A1     Dec. 19, 2013

(51) Int. Cl.
*G01N 21/59*     (2006.01)
*G01N 21/31*     (2006.01)
*G01N 21/80*     (2006.01)

(52) U.S. Cl.
CPC ......... *G01N 21/59* (2013.01); *G01N 21/3151* (2013.01); *G01N 21/80* (2013.01); *Y10T 436/173845* (2015.01); *Y10T 436/196666* (2015.01); *Y10T 436/200833* (2015.01)

(58) Field of Classification Search
CPC ...................................................... G01N 21/59
USPC .......................... 436/119, 131, 164, 166, 178
See application file for complete search history.

(56) References Cited

U.S. PATENT DOCUMENTS

| | | | |
|---|---|---|---|
| 5,710,048 A | 1/1998 | Ernst et al. | |
| 6,017,766 A * | 1/2000 | Holt et al. | 436/164 |
| 6,617,165 B1 * | 9/2003 | Opitz et al. | 436/55 |
| 2004/0185572 A1 * | 9/2004 | Kakuta et al. | 436/86 |

(Continued)

FOREIGN PATENT DOCUMENTS

| | | |
|---|---|---|
| CN | 1200176 A | 11/1998 |
| CN | 1165759 C | 9/2004 |

(Continued)

OTHER PUBLICATIONS

Boyer, Stanton L., et al. "Analytical Method for Nonionic Surfactants in Laboratory Biodegradation and Environmental Studies," *Environmental Science & Technology*, Dec. 1977, vol. 11, No. 13, pp. 1167-1171.

(Continued)

*Primary Examiner* — Krishnan S Menon
*Assistant Examiner* — Dwan A Gerido
(74) *Attorney, Agent, or Firm* — Eric D. Babych; Brinks Gilson & Lione

(57) ABSTRACT

The invention is directed towards methods and compositions for identifying the presence of surfactants in water. The invention is quite superior over the prior art because it can form a colorful complex in half the time, avoid the need for difficult separation steps, use a safer solvent, and avoid the formation of messy foam. The invention involves adding to the water a cobalt thiocyanate reagent, pre-prepared from a cobalt salt and a thiocyanate salt, which forms a colorful complex with the surfactant. Chloroform is then added to the water. The cobalt reagent causes the virtually all of the surfactant to form a colored complex which rapidly migrates into the chloroform and prevents the surfactant from foaming. Once in the chloroform, a UV-vis spectrometer can easily and precisely identify the type and amount of surfactant that was in the water.

18 Claims, 3 Drawing Sheets

(56) References Cited

U.S. PATENT DOCUMENTS

2007/0082004 A1    4/2007   Morton et al.

FOREIGN PATENT DOCUMENTS

| CN | 1816741 A | 8/2006 |
|---|---|---|
| EP | 1382964 A1 | 1/2004 |

OTHER PUBLICATIONS

Greff, R.A., et al. "A Colorimetric Method for the Determination of Parts/Million of Nonionic Surfactants," *The Journal of the American Oil Chemists' Society*, Mar. 1965, vol. 42, pp. 180-185.

Olkowska, Ewa, et al. "Analytics of Surfactants in the Environment: Problems and Challenges," *Chemical Reviews*, 2011, vol. 111, pp. 5667-5700.

\* cited by examiner

METHOD TO MEASURE SURFACTANT IN FLUID

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention relates generally to compositions of matter, apparatuses and methods useful in detecting, identifying, and measuring one or more surfactants in a fluid.

Surfactants are compounds that lower the surface tension in a liquid, lower the interracial tension between two liquid phases in contact with each other in a medium, and/or lower the interfacial tension between a liquid and a solid. Surfactants are amphophilic meaning they contain both hydrophobic groups and hydrophilic groups. This amphophilic character allows surfactants to diffuse in a liquid medium and adsorb at an interphase where two different degrees of hydrophobicity meet. The structure of the surfactant determines how it becomes positioned at the interface and this in turn determines how the surfactant affects the tension at the interface. As a result surfactants are commonly used in environments in which both an aqueous and an organic phase are present.

Surfactants are often polymers and often comprise organic structures. Surfactants often can also function as detergents, wetting agents, emulsifiers, foaming agents, and dispersants. Examples of surfactant compositions include but are not limited to compositions having a net nonionic charge such as those containing alkyl polyglucosides, branched secondary alcohol ethoxylates, ethyl oxide-propyl oxide copolymers (EO-PO), nonphenol ethoxylates, octyphenol ethoxylates, secondary alcohol ethoxylates, siloxanes, and any combination thereof. Some surfactants compositions include net anionic charged compositions such as those containing alkyldiphenyloxide disulfonate salts, dioctyl sulfosuccinates, phosphate esters, sulfates, sulfonates, and any combination thereof.

Surfactants are often used to modulate the interaction between two or more materials existing in one of two or more phases in a medium. As a result it is important to know exactly how much and what kind of surfactant is actually present in a given medium. Too much or too little surfactant may result in too intense or too weak an interaction and can result in undesirable reaction dynamics. Because the dynamic state of many reactions vary, it is difficult to predict how surfactants are consumed or decompose in chemical processes. As a result, even if one knows precisely how much of a given surfactant was previously added to a medium, the exact amount remaining at a given time is not readily discernable.

Thus it is clear that there is definite utility in novel methods and compositions for the proper detection, identification, and measurement of surfactants in a fluid. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed towards a method of detecting and measuring the presence of at least one surfactant in a first liquid. The method comprises the steps of: collecting a representative sample of the first liquid, adding cobalt thiocyanate reagent, pre-prepared from a cobalt salt and a thiocyanate salt, to the sample of the first liquid, allowing the added cobalt thiocyanate reagent to form a colored surfactant bearing complex with substantially all the surfactant in the first liquid, adding a second liquid to the sample, the second liquid being immiscible with the first liquid and being a solvent to the surfactant bearing complex, allowing substantially all of the colored surfactant bearing complex to be extracted into the second liquid, performing a spectrometric measurement of the second liquid, and comparing the spectrometric measurement to pre-determined values to identify the quantity and/or identity of surfactant in the second liquid.

The first liquid may be aqueous. The second liquid may be organic. The second liquid may comprise chloroform. The second liquid may consist essentially of chloroform. The surfactant may be an EO-PO based composition. The spectrometric measurement may involve detecting of absorption peaks of emitted visible and ultraviolet light at about 317 nm. The spectrometric measurement may involve detecting of absorption peaks of emitted visible and ultraviolet light at about 621 nm. The peak at about 317 nm may be greater than the peak at about 621 nm. The spectrometric measurement may involve detecting of absorption peaks at specific pre-determined wavelengths of infrared, visible, and/or ultraviolet light emitted into the second liquid. The intensity of at least one of the detected peaks may be mathematically related to the amount of a specific surfactant present in the first liquid. Substantially all of tile surfactant may be extracted into the second liquid in a single extraction step. The holding time to form a colored surfactant bearing complex may be less than 15 minutes. The method may exclude the addition of foam suppressing salts into the first or second liquid. The method may exclude the presence of methylene chloride, xylene or toluene in the second liquid. The second liquid may be is separated from the first liquid before the spectrometric measurement is performed. The second liquid may comprise a solvent which is non-flammable and which is no more soluble in water than chloroform. The surfactant may comprise at least one item selected from the list consisting of: fluorinated polyoxyethylene surfactant, polyether siloxane surfactant, ethoxylated alkylphenol surfactant, amine and alcohol based polyoxyethylene surfactant, and any combination thereof.

BRIEF DESCRIPTION OF THE DRAWINGS

A detailed description of the invention is hereafter described with specific reference being made to the drawings in which.

DETAILED DESCRIPTION OF THE INVENTION

Figure 1:
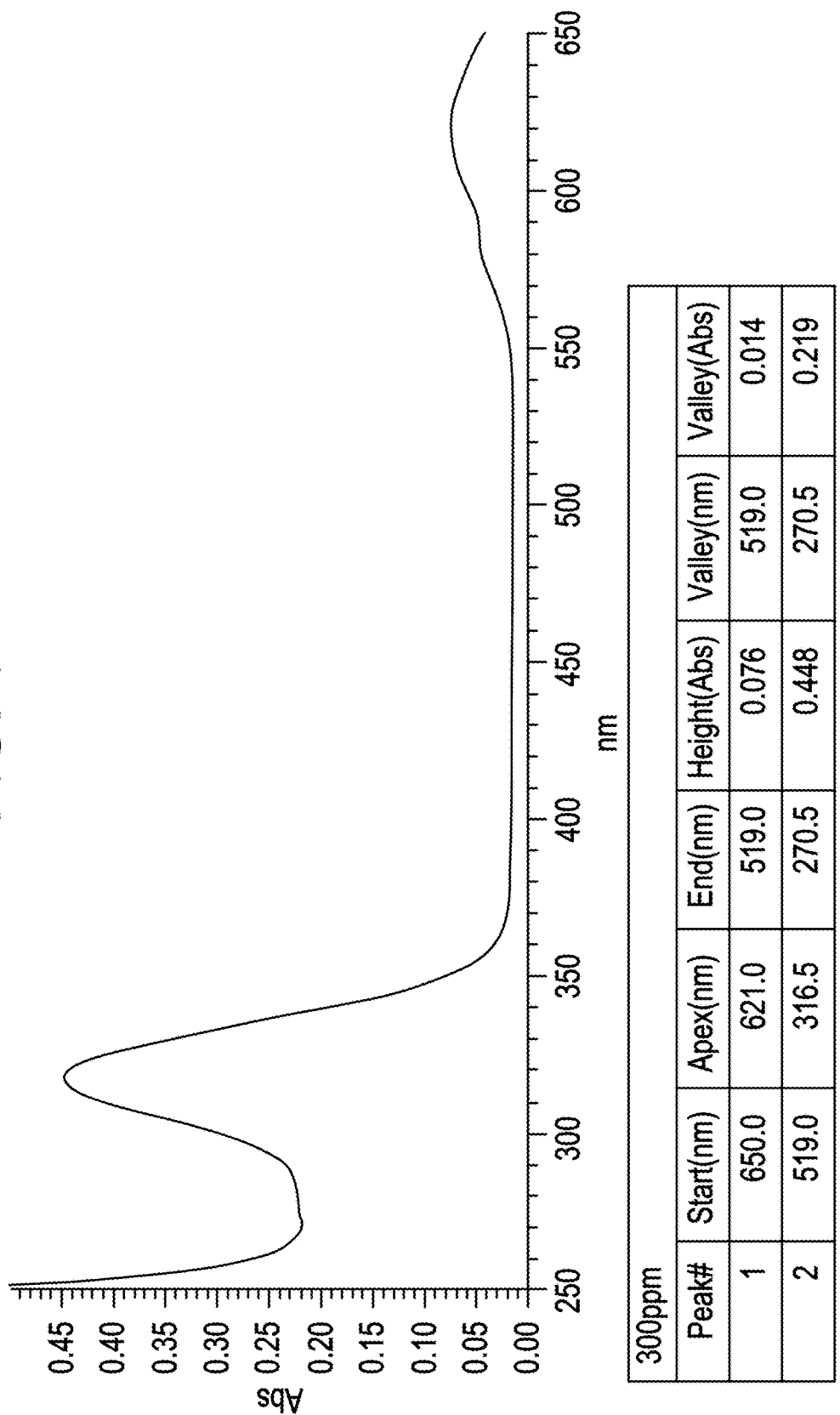
FIG. 1 illustrates a graph of the UV-visible absorbance spectrum for a calibration sample of the invention with 300 ppm of surfactant.

The following definitions are provided to determine how terms used in this application, and in particular how the claims, are to be construed. The organization of the definitions is for convenience only and is not intended to limit any of the definitions to any particular category.

"Alkyl" or "Alkyl Groups" means saturated hydrocarbons having one or more carbon atoms, including straight-chain alkyl groups (e.g., methyl, ethyl, propyl, butyl, pentyl, hexyl, heptyl, octyl, nocyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Unless otherwise specified, the term "alkyl" includes both unsubstituted alkyls and substituted alkyls. In some embodiments, substituted alkyls can include a heterocyclic group.

"Complex" means one or more atoms, typically a metal (the core), bonded to a surrounding array of molecules (the ligands) via one or more bonding mechanisms including coordinate covalent bonds, dipolar bonds, and coordinated pi bonds. Metal complexes often have spectacular colors or have visible or invisible spectroscopic properties caused by electronic transitions in the complex often stimulated by the absorption of light or electromagnetic energy. These transitions often involve d-d transitions, where an electron in a d orbital on the core or ligand is readily excited by a photon to another d orbital of higher energy in an empty ligand or core-based orbital.

"Heterocyclic Group" means a closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

"Liquid-Liquid Separation" means a method to separate one or more compositions of matter based on the compositions' relative solubility in two different immiscible liquids. The different liquids often comprise at least one aqueous solvent liquid (such as water) and at least one organic solvent liquid. The separation often occurs by extracting the compositions from one liquid phase into another liquid phase. The extraction can be facilitated by preferentially dissolving that composition in a suitable solvent or by converting the composition into a compound or a complex matrix that is insoluble or less soluble in one of the two liquids. Techniques for conducting a liquid-liquid separations include but are not limited to batchwise single stage extractions, multistage countercurrent continuous processes, extraetiosn without chemical changes, solvation mechanisms, ion exchange mechanisms, ion pair extractions, aqueous two-phase extractions (including polymer/polymer systems, polymer/salt systems, and ionic liquids systems), and any combination thereof.

"Spectrometry" and "Spectroscopy" means the process of analyzing the interaction between a sample of matter and electromagnetic radiation to determine one or more physical properties of the matter. Forms of electromagnetic radiation used include but are not limited to one or more of microwave, terawave, infrared, near infrared, visible, ultraviolet, x-ray, radiation. The analysis includes measurements of one or more of the radiation's absorption, emission, fluorescence, reflection, scattering, impedance, refraction, and resonance by the material.

"Substituted Alkyls" means alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamide, nitro, trifluoromethyl, cyano, azido, heterocyclic, alkylaryl, or aromatic (including heteroaromatic) groups.

"Surfactant" is a broad term which includes anionic, nonionic, cationic, and zwitterionic surfactants. Enabling descriptions of surfactants are stated in *Kirk-Othmer, Encyclopedia of Chemical Technology*, Third Edition, volume 8, pages 900-912, and in *McCutcheon's Emulsifiers and Detergents*, both of which are incorporated herein by reference.

"Water Soluble" means materials that are soluble in water to at least 3%, by weight, at 25 degrees C.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

At least one embodiment of the invention is directed to a method of detecting the amount of surfactant in a liquid medium. The steps of the method include: adding a reagent composition to the original liquid containing the surfactant and adding a solvent to the liquid. The solvent forms a second liquid phase distinct from that in which the surfactant is located. The reagent comprises cobalt. In at least one embodiment the reagent is prepared by mixing a cobalt salt, like cobalt nitrate, cobalt sulfate, cobalt chloride, cobalt bromide, among others, and any combination thereof and a thiocyanate salt in water. In at least one embodiment the thiocyanate salt is ammonium thiocyanate, sodium thiocyanate, potassium thiocyanate or calcium thiocyanate, and any combination thereof. The cobalt thiocyanate reagent forms a colored complex with the surfactant, which can be quantitatively measured to give the actual concentration of the surfactant in solution. The cobalt thiocyanate reagent facilitates the extraction of the surfactant from the original liquid phase to the newly added liquid phase.

The reagent is so effective at facilitating the extraction of the surfactant that in at least one embodiment the substantially all of the surfactant can be extracted in a single extraction step. In contrast to the invention, in U.S. Pat. No. 6,017,766 the reagent is only added after the surfactant has been extracted from its original solution and this extraction is so difficult that it requires small repeated extractions, preferably performed at least 3 times. In contrast the invention utilizes the reagent as an agent for assisting the extraction so the extraction occurs much more rapidly.

In at least one embodiment the time between adding the cobalt thiocyanate reagent and the formation of a colored complex with the surfactant is less than 15 minutes. In contrast in U.S. Pat. No. 6,017,766, the reagent requires at least 30 minutes to form a colored dye. The faster rate in the invention may be due to the different thermodynamics of the complex reaction occurring in the presence of an aqueous as opposed to only an organic solvent.

Once the colored surfactant complex has migrated to the second liquid phase, one or more spectrometric properties of the second liquid phase are measured. These measurements are then compared to predetermined values known to correspond with the presence and concentration of various surfactants.

In at least one embodiment the at least some of the cobalt salt and at least some of the thiocyanate salt are pre-mixed and are added simultaneously to the first liquid. In at least one embodiment at least some of the cobalt salt is added before at least some of thiocyanate salt.

One advantage of using the reagent composition is that the colored complex is formed before the surfactant is extracted into the second liquid. This prevents the forming of unwanted foam by the surfactant when it contacts the second liquid. Moreover this avoids the need for using salts such as sodium chloride and potassium chloride to de-foam the surfactant.

In at least one embodiment optical properties of the complex are determined through the use of a spectrometer which measures the absorbency of the surfactant complex, and determines the wavelengths at which there are maximum amounts of absorbance.

A pre-determined value for surfactant type and amount can be obtained through the use of calibration curves. In at least one embodiment the samples are prepared by adding known amounts of the surfactant aqueous solutions preferably amounts in the range of the unknown sample. For example if the unknown has an estimated surfactant concentration of 200 ppm, then the standards may range from 0 to 2500 ppm of surfactant. A calibration curve is obtained from the plot of absorbance against concentration of the standard samples. This plot can then be used to give the exact concentration of the sample with the unknown surfactant concentration.

In at least one embodiment the spectrometric analysis used to detect and measure absorption peaks of emitted visible and UV light.

In at least one embodiment the surfactant is an EO-PO based composition and the spectrometric analysis used to detect absorption peaks at 317 nm and 621 nm. In at least one embodiment the peak at 317 nm is more intense than the peak at 621 nm.

In at least one embodiment the first liquid containing the surfactant is water.

In at least one embodiment the second liquid is an organic solvent.

In at least one embodiment the second liquid is chloroform. Chloroform presents several advantages over other organic solvents: promotes an effective extraction of the colored surfactant complex, is a non-flammable solvent and also presents a low solubility in water. Some prior art solvents such as those mentioned U.S. Pat. No. 6,017,766 such as xylene and toluene are flammable, which is not good for safety reasons. Other prior art solvents mentioned U.S. Pat. No. 6,017,766 such as methylene chloride is non-flammable, but its solubility in water is about 16 times higher than chloroform. Since the solvent should not mix with the aqueous phase, chloroform is even more advantageous than methylene chloride.

In at least one embodiment the reagent is added to the first liquid before the second liquid is added. In at least one embodiment the second liquid is not added until after the reagent and the surfactant have completed forming the complex. In at least one embodiment the complex has completely formed in the absence of the second liquid in less than 15 minutes.

In at least one embodiment at least some of the surfactant is extracted from the first liquid into the second liquid via at least one kind of liquid-liquid separation. In at least one embodiment substantially all of the surfactant is extracted from the first liquid into the second liquid via at least one kind of liquid-liquid separation. In at least one embodiment the effectiveness (in terms of at least one of: speed or how complete the extraction was) of one or more liquid-liquid separations was superior due to the addition of the reagent into the first liquid prior to the addition of the second liquid than it would otherwise have been had the second liquid been added before the reagent.

In at least one embodiment the top phase is aqueous and the spectrometric analysis is performed on the bottom phase.

EXAMPLE

The foregoing may be better understood by reference to the following examples, which is presented for purposes of illustration and is not intended to limit the scope of the invention.

In order to obtain a calibration curve, seven calibration samples were prepared at the concentrations 10, 25, 50, 300, 500, 750 e 1000 ppm of an EO-PO based surfactant (Nalco PP10-3340) in distilled water. Each of these samples (6 mL) was put in a glass tube with stopper and 2 mL of the thiocyanate cobalt solution was added to each tube. The thiocyanate solution was prepared by combining 6.2 g of ammonium thiocyanate and 2.8 g of cobalt nitrate hexahydrate in 10 mL of distilled water. The tubes with the sample of surfactant and the cobalt thiocyanate solution were snaked for 1 min and left for 15 min. After that, 4 mL of chloroform was added to these tubes, which were snaked again for another 1 min and left for more 15 min for extraction of the colored surfactant complex into the solvent phase. The top aqueous layer was then removed with a pipette and the absorption of the solvent phase was immediately measured at about 317 nm and at about 621 nm by using an UV-visible spectrometer. In the Example 2 of the U.S. Pat. No. 6,017,766, the solvent phase containing the extracted surfactant was left for 2 hours (after the aqueous layer remotion) before the absorbance measurement.

Figure 2:
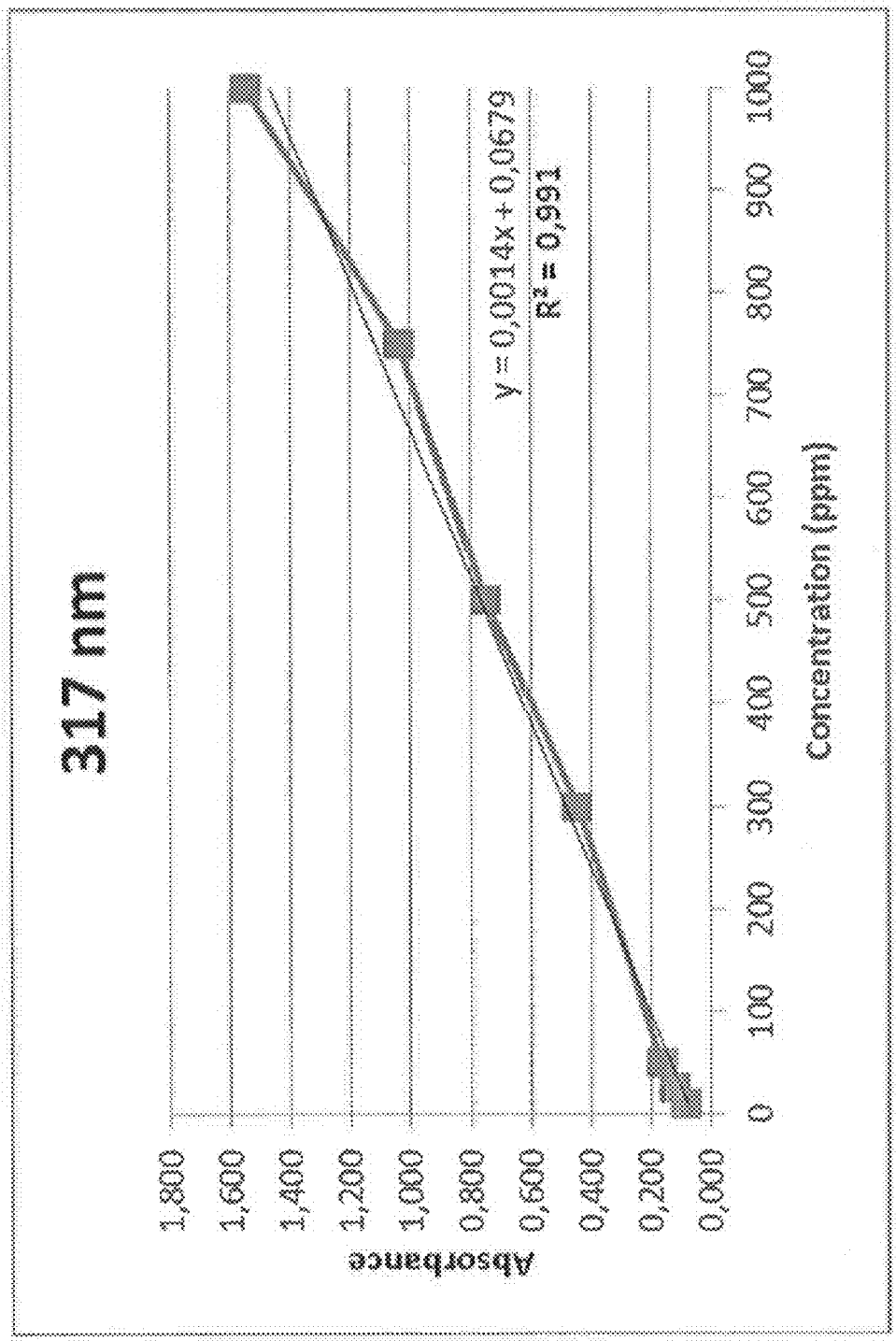
FIG. 2 illustrates a graph of a calibration curve for the invention at an absorbance peak at 317 nm.
Figure 3:
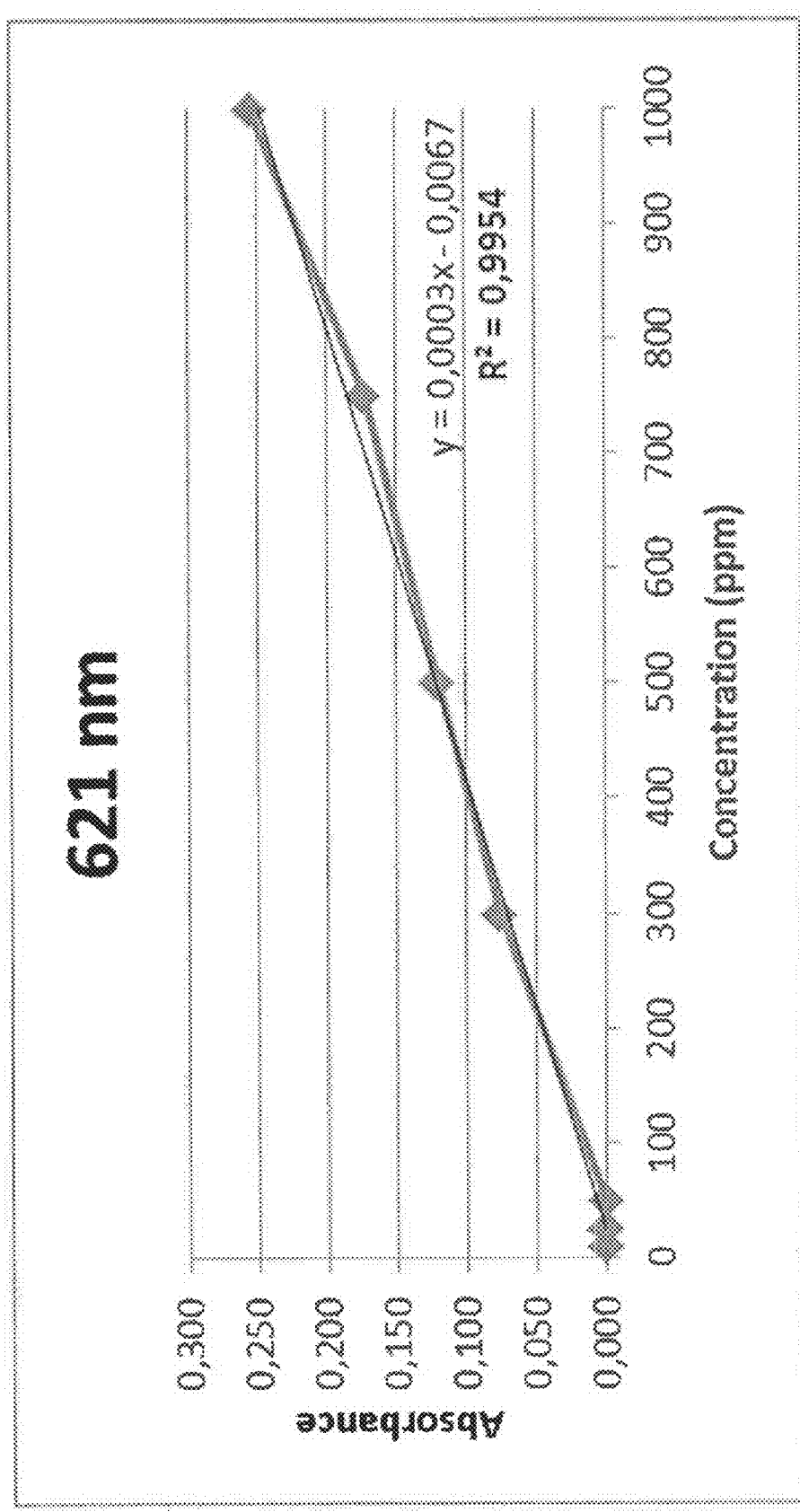
FIG. 3 illustrates a graph of a calibration curve for the invention at an absorbance peak at 621 nm.

As shown in FIGS. 1, 2, and 3, the absorbance values were plotted against the concentration of the calibration samples and the respective correlation coefficients were calculated. This plot can then be used to give the exact concentration of a sample with unknown surfactant concentration. FIG. 1 shows the spectrum obtained for the calibration sample with 300 ppm of surfactant and the calibration curves for the absorbance peaks at 317 nm and 621 nm are shown in FIGS. 2 and 3, respectively. Very good correlation coefficients were obtained, which illustrates that the method of this present invention can be used to accurately measure EO-PO based surfactants concentration in fluids.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and/or incorporated herein. In addition the invention encompasses any possible combination that also specifically excludes any one or more of the various embodiments described herein and/or incorporated herein.

The above disclosure is intended to be illustrative and not exhaustive. This description will suggest many variations and alternatives to one of ordinary skill in this art. The compositions and methods disclosed herein may comprise, consist of or consist essentially of the listed components, or steps. As used herein the term "comprising" means "including, but not limited to". As used herein the term "consisting essentially of" refers to a composition or method that includes the disclosed components or steps, and any other components or steps that do not materially affect the novel and basic characteristics of the compositions or methods. For example, compositions that consist essentially of listed ingredients do not contain additional ingredients that would affect the properties of those compositions. Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure. Weight percent, percent by weight, % by weight, wt %, and the like are synonyms that refer to the concentration of a substance as the weight of that substance divided by the weight of the composition and multiplied by 100.

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of measuring a surfactant in a first liquid, the method consisting of:
   collecting a representative sample of the first liquid wherein the sample of the first liquid consists of water and the surfactant,
   adding a cobalt salt to the sample of the first liquid,
   subsequently adding a thiocyanate salt to the sample of the first liquid, thereby forming a cobalt thiocyanate reagent in the sample of the first liquid,
   allowing the cobalt thiocyanate reagent to form a colored surfactant bearing complex with substantially all the surfactant in the first liquid,
   adding a second liquid to the sample, the second liquid being immiscible with the first liquid and being a solvent to the surfactant bearing complex,
   allowing substantially all of the colored surfactant bearing complex to be extracted into the second liquid,
   performing a spectrometric measurement of the second liquid,
   comparing the spectrometric measurement to pre-determined values to identify the quantity and/or identity of surfactant in the second liquid, and wherein a sodium chloride or potassium chloride salt is not added to the first liquid or the second liquid.

2. The method of claim 1 in which the second liquid comprises or consists essentially of chloroform.

3. The method of claim 1 in which the surfactant is a EO-PO based composition.

4. The method of claim 3 in which the spectrometric measurement involves detecting of absorption peaks of emitted visible and ultraviolet light at about 317 nm and at about 621 nm, the peak at about 317 nm being greater than the peak at about 621 nm.

5. The method of claim 1 in which the spectrometric measurement involves detecting of absorption peaks at specific pre-determined wavelengths of infrared, visible, and/or ultraviolet light emitted into the second liquid.

6. The method of claim 5 in which the intensity of at least one of the detected peaks is mathematically related to the amount of a specific surfactant present in the first liquid.

7. The method of claim 1 in which substantially all of the surfactant is extracted into the second liquid in a single extraction step.

8. The method of claim 1 in which the holding time to form a colored surfactant bearing complex is less than 15 minutes.

9. The method of claim 1 in which the second liquid is separated from the first liquid before the spectrometric measurement is performed.

10. The method of claim 1 in which the second liquid comprises a solvent which is non-flammable and which is no more soluble in water than chloroform.

11. The method of claim 1 in which the surfactant comprises a member selected from the group consisting of fluorinated polyoxyethylene surfactant, polyether siloxane surfactant, ethoxylated alkylphenol surfactant, amine based polyoxyethylene surfactant, and alcohol based polyoxyethylene surfactant.

12. The method of claim 1 in which the complex substantially or completely forms before the second liquid is added to the first liquid.

13. The method of claim 1 in which the formed complex maintains at least some of its colored properties after it migrates into the second liquid.

14. The method of claim 1 in which at least some of the surfactant is extracted from the first liquid to the second liquid via a liquid-liquid separation process.

15. The method of claim 1, wherein the surfactant is fluorinated polyoxyethylene.

16. The method of claim 1, wherein the surfactant is polyether siloxane.

17. The method of claim 1, wherein the surfactant is ethoxylated alkylphenol.

18. The method of claim 1, wherein all of the colored surfactant bearing complex is extracted into the second liquid in a single extraction step.

* * * * *